(12) United States Patent
Yamakawa et al.

(10) Patent No.: US 11,123,557 B2
(45) Date of Patent: Sep. 21, 2021

(54) ELECTRIC STIMULATOR

(71) Applicants: Kensuke Yamakawa, Kuwana (JP);
NIHON MEDIX Co., Ltd., Matsudo (JP)

(72) Inventors: Kensuke Yamakawa, Kuwana (JP);
Norikazu Yoshioka, Matsudo (JP);
Hitoshi Aoki, Matsudo (JP)

(73) Assignees: Kensuke Yamakawa, Kuwana (JP);
NIHON MEDIX Co., Ltd., Matsudo (JP)

( * ) Notice: Subject to any disclaimer, the term of this patent is extended or adjusted under 35 U.S.C. 154(b) by 163 days.

(21) Appl. No.: 15/886,085

(22) Filed: Feb. 1, 2018

(65) Prior Publication Data

US 2018/0154149 A1 Jun. 7, 2018

Related U.S. Application Data

(62) Division of application No. 14/780,368, filed as application No. PCT/JP2014/058054 on Mar. 24, 2014, now Pat. No. 9,919,153.

(30) Foreign Application Priority Data

Mar. 26, 2013 (JP) ................................ 2013-063417

(51) Int. Cl.
*A61N 1/36* (2006.01)
*A61N 1/04* (2006.01)

(52) U.S. Cl.
CPC ....... *A61N 1/36025* (2013.01); *A61N 1/0484* (2013.01)

(58) Field of Classification Search
CPC ............ A61N 1/36175; A61N 1/36157; A61N 1/36164; A61N 1/3628; A61N 1/0529;
(Continued)

(56) References Cited

U.S. PATENT DOCUMENTS

2006/0009815 A1 1/2006 Boveja et al.
2008/0208287 A1 8/2008 Palermo et al.
(Continued)

FOREIGN PATENT DOCUMENTS

GB 2 435 217 8/2007
GB 2 449 546 11/2008
(Continued)

OTHER PUBLICATIONS

Extended European Search Report dated Feb. 5, 2016, directed to EP Application No. 14776311.4; 8 pages.
(Continued)

*Primary Examiner* — Deborah L Malamud
(74) *Attorney, Agent, or Firm* — Morrison & Foerster LLP

(57) ABSTRACT

An electric stimulator that effectively improves the brain function of patients suffering from brain disorders by applying electric stimulation to the brain of the patient effectively. The electric stimulator can include main electrodes H to be stuck to particular sites of the patient's body extending from the neck part to the head tip part. The particular site may be the temple part, the forehead part above the eyes, the cheek part and the rear neck part. The electric signal to be applied to the main electrodes H is set so as for weak electric current of 100 μA or less to flow through the patient's body and stimulate the brain. In addition to the application of electric stimulation by the main electrodes H, auxiliary electrodes S may be stuck to the back of the patient.

4 Claims, 7 Drawing Sheets

(58) Field of Classification Search
CPC .... A61N 1/36167; A61N 1/04; A61N 1/0526; A61N 1/36146; A61N 1/32; A61N 1/3615; A61N 1/36178; A61N 1/3987; A61B 5/4836; A61B 5/4064; A61B 5/486; A61B 5/02; A61B 5/6868; A61B 5/7282

See application file for complete search history.

(56) References Cited

U.S. PATENT DOCUMENTS

| | | | |
|---|---|---|---|
| 2011/0093032 A1* | 4/2011 | Boggs, II | A61N 1/3611 607/42 |
| 2012/0226333 A1 | 9/2012 | Szeles | |
| 2012/0303080 A1 | 11/2012 | Ben-David et al. | |

FOREIGN PATENT DOCUMENTS

| JP | 2009-153904 A | 7/2009 |
|---|---|---|
| JP | 2009-531154 A | 9/2009 |
| JP | 2010-519003 A | 6/2010 |
| JP | 2011-517962 A | 6/2011 |
| JP | 2012-509121 A | 4/2012 |
| JP | 2013-31708 A | 2/2013 |
| JP | 2013-506535 A | 2/2013 |

OTHER PUBLICATIONS

Yamakawa et al., U.S. Office Action dated Jul. 28, 2016, directed to U.S. Appl. No. 14/780,368; 9 pages.

Yamakawa et al., U.S. Office Action dated Feb. 13, 2017, directed to U.S. Appl. No. 14/780,368; 10 pages.

Yamakawa et al., U.S. Office Action dated Jul. 25, 2017, directed to U.S. Appl. No. 14/780,368; 9 pages.

International Search Report dated Apr. 15, 2014 directed towards International Application No. PCT/JP2014/058054; 2 pages.

International Preliminary Report on Patentability and Written Opinion dated Sep. 29, 2015 directed towards International Application No. PCT/JP2014/058054; 5 pages.

* cited by examiner a temple part a forehead part above the eyes a cheek part a rear neck part

ELECTRIC STIMULATOR

CROSS-REFERENCE TO RELATED APPLICATIONS

This application is a divisional of U.S. patent application Ser. No. 14/780,368, filed Sep. 25, 2015, which is a national phase filing under 35 U.S.C. § 371 of International Application No. PCT/JP2014/058054, filed Mar. 24, 2014, and which claims priority to Japanese Patent Application No. 2013-063417, filed on Mar. 26, 2013, the entire contents of each of which are incorporated herein by reference.

FIELD OF THE INVENTION

The present invention relates to an electric stimulator useful for improvements in brain disorders.

BACKGROUND OF THE INVENTION

Various brain diseases are known which may be caused particularly by an underdeveloped or ill-developed neural network. Focusing on the fact that patients with underdeveloped or ill-developed brain functions may have the underdeveloped or ill-developed thenar and an abnormal sense of the digit, Patent Document No. 1 discloses an electric stimulator for stimulating the brain of a patient to improve the brain dysfunction by intermittently transmitting electric signals to the brain of the patient by means of the electrodes stuck on the thenar and the digit of the patient.

PRIOR ART REFERENCES

Patent Document No. 1: Japanese Patent Application Publication No. 2009-153904 (U.S. Pat. No. 5,053,826)

SUMMARY OF THE INVENTION

The prior art electric stimulator as disclosed in Patent Document No. 1 may be expected to have effects on a recovery of the brain dysfunction, but has limited effects on the electric stimulation from the peripheral nerve. Further improvements in the electric stimulator are needed.

The present invention has been performed with the above background taken into consideration and has an object to provide an electric stimulator which can effectively improve the brain dysfunction by stimulating the brain efficiently.

In order to achieve the above object, the present invention provides an electric stimulator for applying an electric signal to the body of a patient through an electrode, which comprises a main electrode to be stuck to a particular site of the body of a patient extending from the neck part to the head tip part so as to apply stimulation to the brain without passage through the brain stem; wherein the electric signal to be applied to the main electrode is set for a weak electric current stimulating the brain to flow through the body of the patient; wherein the weak electric current is applied by repeating a predetermined cycle; wherein the predetermined cycle comprises a first state and a second state, the first state in which the application of the weak electric current is continued for a fixed period of time, and the second state in which the application of the weak electric current is ceased after the first state for a period of time equal to or longer than the fixed period of time for the first state; wherein the application of the weak electric current in the first state is performed to increase the weak electric current gradually toward a predetermined current value and then maintain the predetermined current value for a period of time longer than the period of time during which the application of the weak electric current is being increased gradually; and wherein the timing of applying the electric signals to a plurality of the main electrodes is set to shift gradually from synchronization and then synchronize again in a constant cycle.

The present invention provides the solution to the disadvantages of the prior art electric stimulators and can improve the brain dysfunction effectively because the electric stimulator of the present invention enables the electric signal to stimulate the brain directly by bypassing the brain stem without passage through the peripheral nerves.

The electric stimulator according to the present invention is preferred in terms of being capable of applying an adequate amount of electric stimulation to the brain as a whole because it can apply an appropriate stimulation to the brain and prevent the brain from being exhausted by ensuring a sufficient cease time. Moreover, it is preferred in terms of being capable of preventing a rapid stimulation of the brain as well as applying a satisfactory amount of electric stimulation to the brain as a whole without causing the brain to become exhausted.

In addition to the foregoing, the electric stimulator according to the present invention is preferred in terms of being capable of further enhancing the therapeutic effects by diversifying manners of stimulation application. It is particularly preferred to apply stimulation at a stage at which the therapeutic effects have advanced.

Given the above solution, preferred embodiments of the present invention are as will be described.

In a preferred embodiment of the present invention, the particular site of the patient's body at which the main electrode is stuck is defined by at least one site selected from the temple part, the forehead part above the eye, the cheek part, and the rear neck part. This embodiment provides a preferred site or sites for sticking the main electrode for application of a direct stimulation to the brain.

In another preferred embodiment of the present invention, the particular sites of the patient's body for the main electrodes are selected from plural sites, i.e., at least two sites, selected from the temple part, the forehead part above the eye, the cheek part, and the rear neck part. This embodiment is preferred in terms of enhancing improved effects on the treatment of the brain dysfunction by optionally increasing the number of the particular sites, i.e., two, three, or all four, to which the main electrodes are stuck.

A further preferred embodiment of the present invention provides a mounting means of a headgear type for covering the head of a patient, which is equipped with the main electrodes on the inner face of the mounting means so as to come into contact with the particular sites of the patient's body, that is, the plural sites selected from the temple part, the forehead part above the eye, the cheek part, and the rear neck part of the patient, respectively, upon covering with the head of the patient with the mounting means. This embodiment enables the main electrodes to be mounted simultaneously at the plural particular sites of the patient's body.

In a still further preferred embodiment of the present invention, the weak electric current has a frequency of 10 to 80 pps (pulse per second) and an electric current value from 10 μA to 100 μA. This embodiment provides a specific range of application of the weak electric current. If the frequency would become too large, the brain may make it difficult to distinguish each one of electric signal pulses so that the frequency is preferred to be smaller than 80 pps. If the frequency would become too small, the number of pulses per unit time to be transmitted to the brain may become too small so that the frequency is preferred to be higher than 10 pps. On the other hand, if the current value would become too high, stimulation to the brain may become too high so that the current value of smaller than 100 μA is preferred, while the current value of higher than 10 μA is preferred because, if it would become too small, the brain may not sense stimulation effectively and the amount of stimulation to the brain may become too small.

The present invention provides a preferred embodiment of the weak electric current, wherein the frequency is set to from 20 to 60 pps and the electric current value is set to from 20 μA to 80 μA.

In a still further embodiment of the present invention, the application of the weak electric current in the first state is performed by alternately repeating a plus application and a minus application. This embodiment may help the patient in preventing a state of feeling pain at the site on which the main electrode is stuck.

In a still further embodiment of the present invention, the weak electric current is applied in the first state in a cycle always by either of the plus application or the minus application in such a manner that the plus application and the minus application are exchanged for each other alternately. More specifically, when the application of the weak electric current is performed in the first state in a previous cycle by the plus application, then the application of the weak electric current is performed in the next first state in the next cycle by the minus application, and vice versa. This embodiment can achieve the effects similar to those achieved by the embodiment.

In order to achieve the above objects, the present invention adopts the alternative solutions as will be described below.

The present invention in an embodiment provides an electric stimulator for applying an electric signal to the body of a patient through an electrode, comprising a main electrode to be stuck to a particular site of the patient's body extending from the neck part to the head tip (vertex) part for stimulating the brain without passing through the brain stem, wherein the electric signal to be applied to the main electrode is set to flow a weak electric current through the body of the patient to stimulate the brain; the weak electric current is applied by repeating a predetermined cycle; the predetermined cycle comprises a first state and a second state, the first state being a state in which the application of the weak electric current is continued for a predetermined period of time and the second state being a state in which the application of the weak electric current is ceased after the first state for a period of time equal to or longer than the predetermined period of time during which the application of the weak electric current is continued; the weak electric current is applied in the first state so as to increase gradually toward a predetermined electric current value and then maintained at the predetermined electric current value for a period of time during which the weak electric current is increasingly applied; an auxiliary electrode is further provided, which is stuck on a site in a half of the body of the patient lower than the neck; an electric signal to be applied to the auxiliary electrode is set for a stimulating electric current larger than the weak electric current so as to flow through the patient's body; and the timing of applying the electric signal to the main electrode and the auxiliary electrode is set so as to shift gradually from synchronization and synchronize again in a constant cycle. This embodiment is preferred in order to further obtain the satisfactory effects corresponding to those as obtained by the invention by stimulating the brain through the peripheral nerves. Particularly, this embodiment is preferred particularly to further promote the therapeutic effects by diversifying manners of stimulations, especially to apply stimulation at advanced stages.

In a still further embodiment of the present invention, the auxiliary electrode is stuck on the back of the patient so as to stimulate the brain through the spinal cord. This embodiment can provide the electric signal to the spinal cord sensitive among the peripheral nerves, thereby preferably demonstrating the adequate effects corresponding to those achieved by the embodiment.

In a still further embodiment of the present invention, plural pairs of the auxiliary electrodes to which the electric stimulation is applied simultaneously are stuck on the patient's back in a spatial relationship across the spine in an up-and-down direction. This embodiment is preferred in order to further demonstrate the effects to such an adequate extent as achieved by the embodiment.

In a still further embodiment of the present invention, the weak electric current is set to from 10 μA to 100 μA, and the stimulating electric current is set to from 30 mA to 300 mA. This embodiment can provide the preferred scopes of the weak electric current values of the electric signal and the stimulating electric current.

The present invention can achieve improvements in the brain dysfunction effectively.

DETAILED DESCRIPTION OF THE INVENTION

Figure 1:
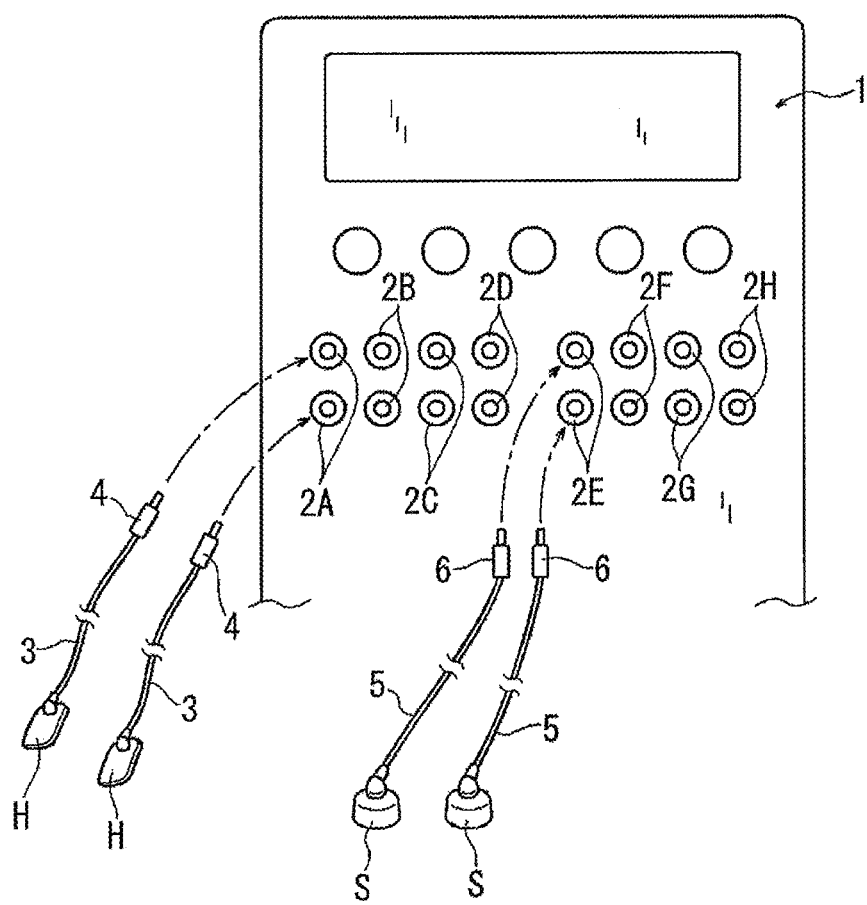
FIG. 1 is a simplified perspective view showing an example of the electric stimulator according to the present invention.

As shown in FIG. 1, reference numeral 1 represents a main body of an electric stimulator according to the present invention. The main body 1 is provided with a total number of eight channels, four being for the main electrodes H and the other four channels for an auxiliary electrodes S. Each channel comprises a pair of output parts 2A to 2H, respectively, on the plus side and the minus side. More specifically, each of the four channels for the main electrodes H consists of a pair of output parts 2A to 2D, respectively, and each of the four channels for the auxiliary electrodes S consists of a pair of output parts 2E to 2H, respectively. The main electrode H may be of a sheet type, and the auxiliary electrode S may be of a plunger type. In FIG. 1, both of a pair of the main electrodes H and a pair of the auxiliary electrodes S are shown only for the output parts 2A and 2E, respectively.

The main electrode H is connected to a connecter 4 through a cable 3, and the connecter 4 is in turn connected detachably to a pair of the output parts 2A to 2D, respectively, transmitting electric signals to the main electrodes H. Similarly, the auxiliary electrode S is connected to a connecter 6 through a cable 5, and the connecter 6 is in turn connected detachably to a pair of the output parts 2E to 2H, respectively, transmitting electric signals to the auxiliary electrodes S.

Figure 2:
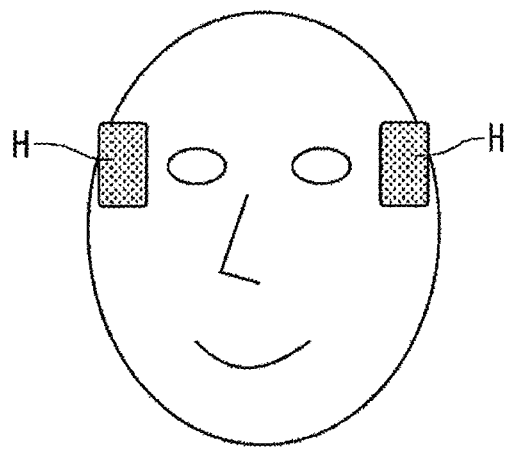
FIG. 2 is a simplified front view showing an example of a pair of main electrodes stuck on the temple part of a patient.
Figure 3:
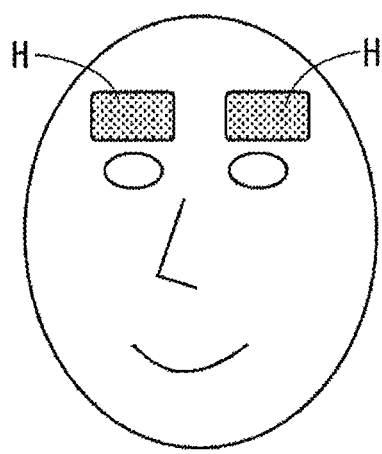
FIG. 3 is a simplified front view showing an example of a pair of main electrodes stuck on the forehead part above the eyes of a patient.
Figure 4:
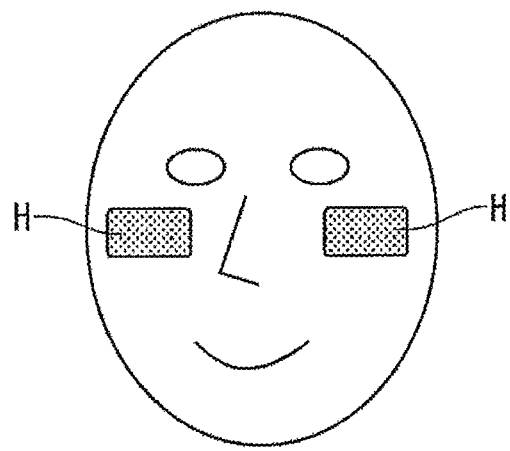
FIG. 4 is a simplified front view showing an example of a pair of main electrodes stuck on the cheek part of a patient.
Figure 5:
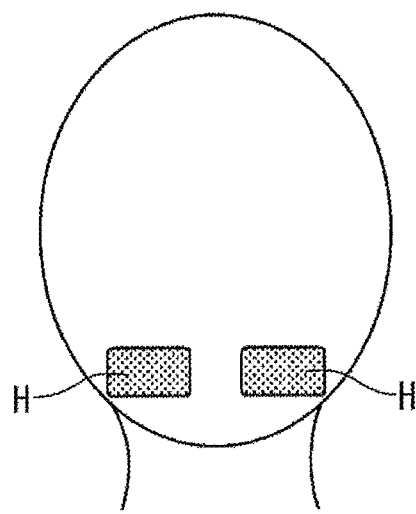
FIG. 5 is a simplified rear view showing an example of a pair of main electrodes stuck on the rear neck part of a patient.

The main electrodes H may be stuck to a site of the body of a patient extending from the neck part to the head tip part. More specifically, the main electrodes H may be stuck to a particular site of the patient's body at which electric signals are applied directly to the brain and stimulate the brain without the passage through the peripheral nerves, i.e., without causing any decrease in stimulation by the brain stem. More specifically, an example of a pair of the main electrodes H stuck to the left and right temple parts of a patient is shown in FIG. 2. An example of a pair of the main electrodes H stuck to the left and right forehead parts above the eyes of a patient is shown in FIG. 3. An example of a pair of the main electrodes H stuck to the left and right cheek parts of a patient is shown in FIG. 4. An example of a pair of the main electrodes H stuck to the rear neck part of a patient is shown in FIG. 5. The main electrodes H may be optionally stuck to the rear parts of the left and right ears or other parts of a patient.

Figure 6:
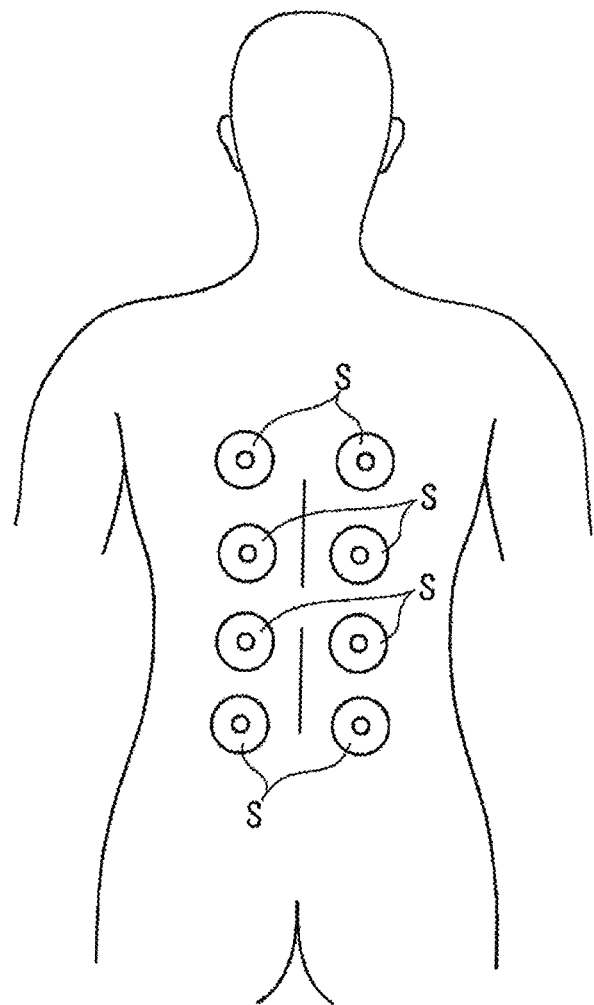
FIG. 6 is a view showing an example of plural pairs of auxiliary electrodes stuck on the patient's back along and between the spinal cord.

The auxiliary electrodes S may be stuck on a site on the part of the patient's body lower than the neck at which the brain can be stimulated by electric signals through the peripheral nerves while undergoing the action of decreasing stimulation to the brain by the brain stem barrier. FIG. 6 shows an example in which a total number of four pairs each consisting of the left and right auxiliary electrodes S is stuck in a spatial relationship on the right and left sides of the patient's back between and along the spinal cord. The spinal cord is sensitive among the peripheral nerves and has a large capacity of transmittal of stimulation so that it is a favorite site for stimulating the brain by the auxiliary electrode S. The auxiliary electrode S may be stuck, for example, to the fingertip, the ball of the foot, the digit and any other appropriate part of the patient's body.

Figure 7:
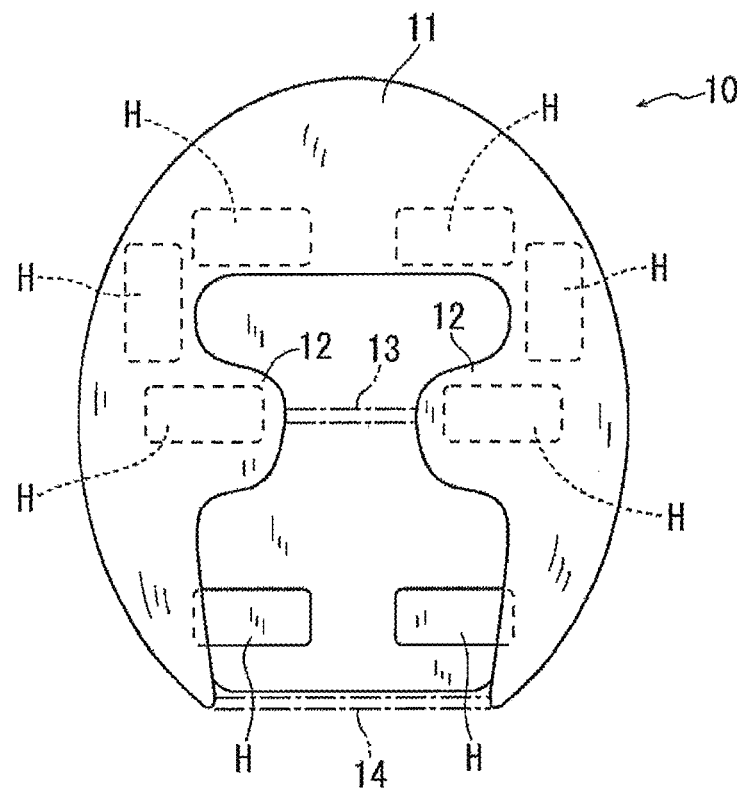
FIG. 7 is a front view showing a mounting means of a headgear type with main electrodes equipped.

FIG. 7 shows an example of a mounting means 10 designed to be suitable particularly for attaching plural pairs of the main electrodes H to the four sites as indicated in FIGS. 2 to 5. The mounting means 10 may be of a headgear type and be made, for example, from an elastic sheet material in order to permit a tight covering of the patient's head. As shown in FIG. 7, the mounting means 10 may comprise a main body part 11 of a hood shape for covering the head and the neck of the patient, with the front side (the face side of the patient) formed open to expose the eyes, the nose and the mouth of the patient to the outside. The mounting means 10 may cover the head tip part, the left and right side face parts and the rear head part as well as the upper neck part of the patient. The main body part 11 may be provided with a pair of left and right extension parts 12 extending from the positions somewhat below the eyes toward the nose so as to cover the left and right cheek parts of the patient's face. As shown in FIG. 7, the main electrodes H may be equipped on the inner face of the mounting means 10 at the positions corresponding to the particular sites of the patient's head and neck as shown in FIGS. 2 to 5, respectively. More specifically, the positions of the mounting means 10 corresponding to the forehead parts, the temple parts and the cheek parts are indicated by dashed lines, and the positions thereof corresponding to the rear neck parts are indicated by solid and dashed lines. They may be mounted in a fixed manner or a detachable manner with, for example, a Velcro fastener.

Figure 8:
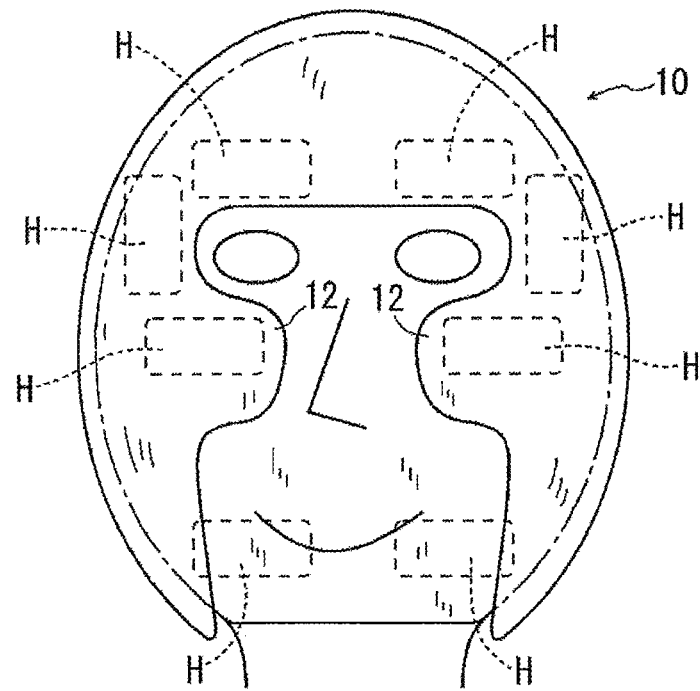
FIG. 8 is a front view showing a state in which the mounting means of FIG. 7 is stuck on the patient's head.

FIG. 8 indicates a state in which the mounting means 10 as shown in FIG. 7 covers the head and the upper neck of a patent. The main electrodes H are equipped on the inner face of the mounting means 10 at the positions, as indicated by the dashed lines, in such a manner that they can be aligned with and correspond to the particular sites of the patient's head and neck as indicated in FIGS. 2 to 5, respectively, as the patient's head and neck are covered with the mounting means 10. The mounting means 10 ensures a close attachment of the main electrodes H to the patient at the particular sites as indicated in FIG. 8. The left and right extension parts 12 may be connected to each other by an elastic string 13, and the bottom side edge parts of the left and right extension parts 12 may also be connected to each other by an elastic string 14. The connection of the left and right extension parts 12 by the elastic strings 13 and 14 also help the mounting means 10 to come into close attachment with the patient's head and neck by means of the elastic force of the elastic strings as the patient's head and neck are covered with the mounting means 10. The left and right extension parts 12 may be equipped inside with a thin elastic plate in order to allow the extension parts 12 to come into close attachment with the cheek parts of the patient's face by means of the elastic force of the thin elastic plate.

In a working mode, four pairs of the main electrodes H may be stuck to those sites as indicated in FIGS. 2 to 5 using the mounting means 10 as shown in FIG. 8, and four pairs of the auxiliary electrodes S may also be stuck to the patient's back as shown in FIG. 6. In such a state as indicated herein, the electric signals are applied so as to pass the weak electric current through the patient's head by means of the main electrodes H. Similarly, the electric signals may be applied so as to pass the stimulating electric current through the patient's body by means of the auxiliary electrodes S. Each of the electric signals are generated by the main body 1 of the electric stimulator as shown in FIG. 1 and outputted from the output parts 2A to 2H, respectively.

The main electrodes H can give stimulation directly to the brain. In this embodiment, the electric stimulation may be applied separately or simultaneously from four different sites to effectively stimulate the brain and reconstitute a neural network of the brain, resulting in effective improvements in the brain dysfunction. In addition to the stimulation by the main electrodes H, the stimulation to the brain may also be performed by the auxiliary electrodes S through the peripheral nerve. This may also promote the reconstitution of a neural network resulting in effective improvements in the brain dysfunction.

Figure 9:
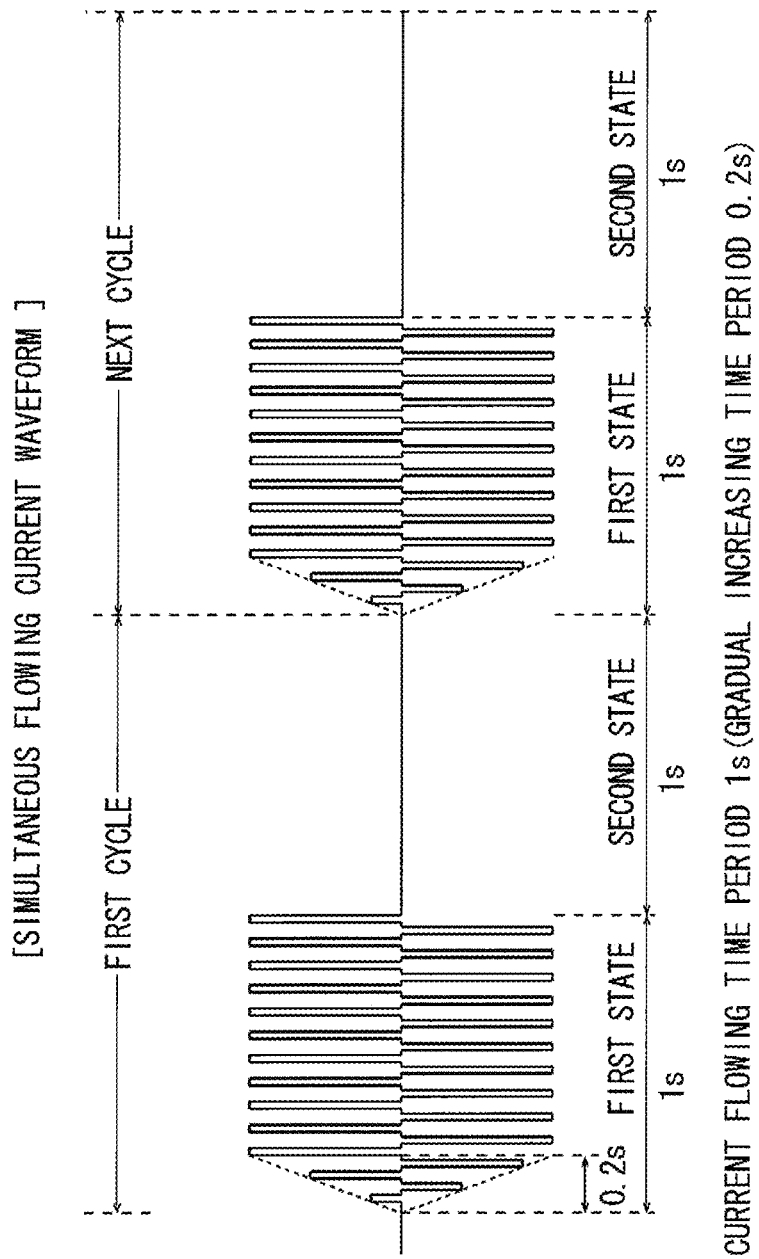
FIG. 9 is a characteristic view showing a specific example of electric signals to be applied to the main electrode.

A more detailed description will now be made regarding the electric signals to be applied to the main electrodes H. FIG. 9 shows an example of a manner of simultaneous current flowing of electric signals in a flowing current waveform. In the example of FIG. 9, there is shown an embodiment in which the predetermined cycles are repeated. The predetermined cycle may be largely broken down into a first state and a second state, the first state being a state in which the application of stimulation is continued for a fixed period of time (e.g., 1 second in FIG. 9) and the second state being a state in which the application of the electric signal is ceased for a period of time equal to or longer than the above fixed period of time (1 second in this working embodiment) after the first state. The next cycle may start after the elapse of the second state in the previous cycle.

The duration of the second state may be set to be equal to or longer than the predetermined time of the first state and set twice or more the predetermined time thereof. In particular, from the viewpoint of prevention of exhaustion of the brain, the time of the second state may be altered as needed. The cease time in the second state is important and it is desired to ensure a sufficient long time in order for the brain to fail to feel tired. This can also be true of the transition time to the next cycle.

In the first state, the electric signals may be applied in such a manner that plus and minus pulses are generated alternately. This may prevent pain from being felt at the sites at which the main electrodes H are stuck. The frequency of the electric signal in the form of pulse wave may be set in the range of from 10 to 80 pps (pulse per second) and 50 pps in this working embodiment. In order to allow the brain to perceive one pulse, it is preferred to set the frequency to 80 pps or smaller, preferably 60 pps or smaller. If the frequency would be smaller, it is difficult to give sufficient numbers of stimulations so that the frequency may be set to 10 pps or larger, preferably 20 pps or larger. In this embodiment, the frequency is set to 50 pps. The waveform as shown in FIG. 9, however, is shown by the pulse numbers smaller than the actual pulse numbers at 50 pps in order to represent the waveform in more detail. This is the same as in FIG. 10.

The magnitude (voltage) of the electric signals to be applied to the main electrodes H may be set so as for the weak electric current to flow through the patient's body in the range of 1 mA (1,000 μA) or less, more specifically 100 μA or less. If the electric current value would be a larger value over 100 μA, the stimulation to the brain may become too great. It is preferred, accordingly, that the electric current value be set to 100 μA or less, preferably 80 μA or less. If the electric current value would become too small, then the brain may not perceive it so that it is preferred to set it to 10 μA or higher, preferably 20 μA or higher. In this example, it is set to 40 μA.

In the example of FIG. 9, the electric current value in the first state may be further set to become increasing gradually from zero to reach a constant predetermined electric current value and maintain this value for a period of time longer than the time period set in the first state. For example, the time period during which the electric current value is being gradually increased in the first state may be set to last 0.2 second while the time period during which the electric current value is maintained at the constant value may be set to last 0.8 seconds. The time period for maintaining the predetermined electric current value is set preferably to become sufficiently longer than the time period for gradually increasing the electric current value. The reason for gradually increasing the electric current value is to avoid a rapid application of the stimulation to the brain.

Figure 10:
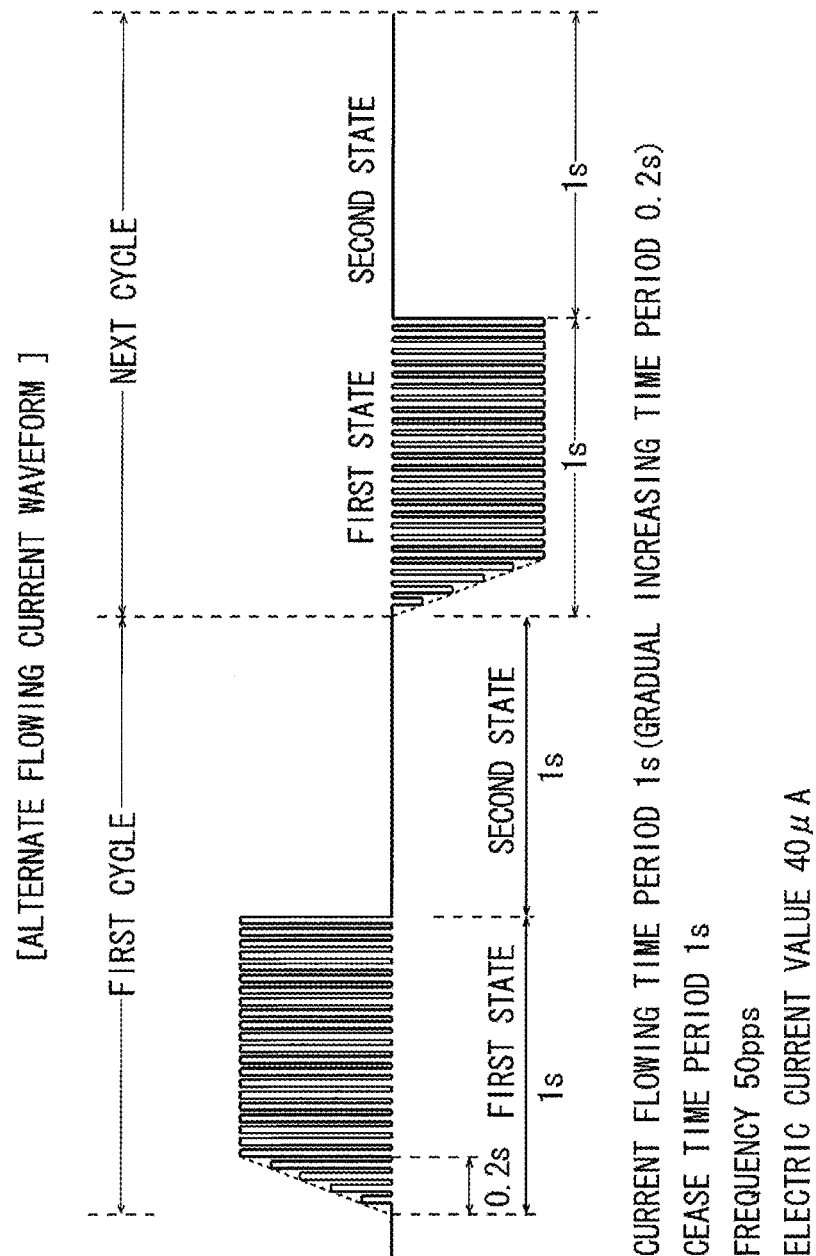
FIG. 10 is a characteristic view showing another specific example of electric signals to be applied to the main electrode.

FIG. 10 shows a variant of FIG. 9, in which the predetermined cycle comprises the first state during which to apply the electric signals and the second state during which to cease the application of the electric signals, similarly to the case of FIG. 9. FIG. 10 is different from FIG. 9, however, in that pulses on the plus side only are applied in the first state in the previous cycle, while pulses on the minus side only are applied in the first state in the next cycle, and vice versa. This mode of the application of the electric signals allows the electric signals to change between plus and minus pulses alternately whenever the cycles are changed. Other conditions such as frequency, electric current value and so on may be set in substantially the same manner as in FIG. 9.

The electric signals to be applied to the auxiliary electrodes S may be appropriately applied in such a range as the stimulation is perceivable by the brain. It should be noted herein, however, that the electric current value to be applied to the auxiliary electrodes S may be set to become sufficiently larger than the weak electric current applied to the main electrodes H because the electric signals to be applied by the auxiliary electrodes S stimulate the brain through the peripheral nerves. The electric current value to be applied by the auxiliary electrodes S may range, for example, from 30 mA to 300 mA. The application of the stimulation from the auxiliary electrodes S corresponds to or synchronizes with the application of the stimulation from the main electrodes H. In another words, the manner of the application of the electric signals to the auxiliary electrodes S may be basically the same as the electric signals to the applied to the main electrodes H, although only the electric current values differ largely from those of the main electrodes H. The conditions including the frequency, the time period of the first state, the time period of the second state, and so on are set to be the same as in FIG. 9 and FIG. 10.

The following is a supplemental description regarding the present invention from the medical point of view. First, the somatic sensation consists of cutaneous sensation and deep sensation. The cutaneous sensation may be broken down into tactile sensation, pressure sensation, pain sensation, and temperature sensation (including warm and cold sensation). The deep sensation may be broken down into deep pain sense, vibration sense, and sensation of joint (including a sense of movement and a sense of position). For normal healthy newborn babies and infants, a development of the somatic sensation appears in association with an intellectual development. In particular, the development of the deep sensation among the somatic sensation is so rapid that, up to an age of approximately 1 year, the head control, turning over, crawling on all fours, sitting, standing, and walking at standing appear in order. Moreover, infants may start pronouncing simple, but meaningful words at that age. It is considered that, for babies and infants, the extrapyramidal tract develop leading to an appearance of functions including an act of speaking and so on. This implies the possibility that no intellectual development could appear without any development of the extrapyramidal tract. Recently, it has been proposed that the neural network changes from an immature type to a mature type in accompaniment with a development of the brain tissue (Baby Science, vol. 8, pp. 26-36, 2008). As an example of an immature neural network, there may be mentioned newborn babies, and the immature neural network may be reorganized to the mature neural network type as the babies grow. In the neural network of the brain tissue of the immature type, an afferent stimulation does not accurately reach the neurons of question as shown in the mature type, however, the afferent stimulation may accurately reach the neurons of question as the brain tissue is becoming mature for normal healthy infants. At this time, the neurons are inhibited to such an extent to which no afferent stimulation is transmitted to other neurons (Baby Science, vol. 8, pp. 26-36, 2008). Infants with brain disorder are considered that no neural network may be reorganized.

Down's syndrome is a disease associated with the brain disorder, and cases where the mobility of the joints is enhanced in infants with the Down's syndrome are recognized in no small numbers. This is a floppy infant-like symptom in many cases, which is characterized by frog position, wet towel-like phenomenon, scarf phenomenon, or double folding (The Journal of The Japan Medical Association, Vol. 125, No. 8, p. 12). In floppy infants, there is a phenomenon that may be seen as a result of the enhanced mobility of the joints and, particularly, the double folding is considered to be largely associated with the mobility of the joints of the spine. In the case like this, it is considered that the deep sensation is not yet established and the neural network involved in the deep sensation is not reorganized to the mature type. As the deep sensation is maintained by the extrapyramidal tract, this belongs to a region of unconsciousness in the field of brain function. Infant patients showing such a phenomenon indicate that the region of unconsciousness of the brain does not hold its function.

The electric stimulation to the hands and the feet by a low frequency is useful for improvements in symptoms of patients with hearing disorders, brain disorders, cerebral infarction, vision damages, or the like. On the other hand, for patients suffering from brain disorders such as Down's syndrome, the electric stimulation by a low frequency may help in improving the speaking function, reading abilities, rhythm accompaniment abilities, or the like. This is considered to improve these functions due to the phenomena that the current flow from the peripheral nerves promotes the reorganization of the neural network. As the effects of the current flow from the peripheral nerves are limited, however, the electric stimulation by low frequencies cannot solve the intellectual dysfunction of the Down's syndrome fundamentally. Now that the present inventors have come to the idea from this result that there might be some problems with procedures for applying an electric stimulation to the brain, therefore, they have focused on the electric current and the site for stimulation by changing the electric current to weak electric current and targeting the almost whole area of the patient's body, except for the hands and the feet, for sticking the electrodes, particularly the head part above the neck part at which the brain can be stimulated directly.

Case #1 for a patient with initials YM (female, 14 years old): The following is the result of a specific investigation of abnormality of cutaneous sensation. In this patient, hypaesthesia was recognized at the posterior surface on both sides of the thigh (corresponding to the sacral vertebrae I and II), and she had a characteristic facies of the Down's syndrome, which was poor in development of the mimetic muscles of her face and was considered to accompany perceptual disorders. From these symptoms, these sites were decided to be targeted for electric stimulation. Moreover, the electric stimulation was carried out as simultaneously as possible because, as the neural network could not be reorganized toward maturation unless the electric stimulation would be applied to the sensory nerves, the maturing of the neural network was considered likely to occur when information is transmitted to many nerves. More specifically, the electric stimulation was conducted by sticking a gel electrode having a size of 5 cm by 9 cm to the sites on both sides of the spine extending from the sacral nerve IV to the cervical vertebrae IV according to the segments of the cutaneous nerves. To the face, a 5 cm×9 cm gel electrode was stuck on both sides of the face in such a manner that the top edge of the gel electrode became at most in touch with the zygomatic arch. The weak electric current of 30 µA was sent for 15 minutes to the gel electrodes from the left side to the right side across the spine and the cranial bone. The electric current was started up at 0.5 s to a steady-state current and sustained for 1 second, followed by discontinuation of the current flow. After 1.5 seconds, the positive pole and the negative pole were exchanged between the left and right sides, and the weak electric current was started up at 0.5 s to the steady-state current level and continued to flow the steady-state current for 1.0 second, followed by discontinuation of the current flow and suspension for 5 seconds. A series of these operations was set as one course of operations, and the weak electric current was sent for 15 minutes from the peripheral nerves to the neural network in accordance with these operations.

At day 1 of the start of this treatment, her mother said to her, "I will go to a video shop to return a video tape I borrowed", then, she replied "I would also like to return a video tape". Further, her mother asked her, "Until when has the video tape be returned?" Then, she replied, "the tape has to be returned till today." Before then, she has never replied to such questions. This implied that she would be likely to begin developing a time concept after treatment.

At day 3 after the start of treatment, she showed changes in abilities of counting numbers of persons on a TV as "one person", "two persons", "three persons", and so on. Nothing of this ability was recognized in her before. Moreover, she claimed as being ticklish on peeling off the gel electrodes from her back. At day 8 after treatment, she could begin to read mathematical sentence problems by herself and answer them. After 30 days, her posture of sitting was improved better.

After 35 days, she could begin to make a simple subtraction such as "six minus one", "ten minus five", or the like. After 42 days, she could copy and transcribe an initial part of a Japanese textbook of a first grade in elementary school. At these days, she could also begin able to handle a "karaoka" machine alone without any help of other persons. After 47 days, she asked the way of pronouncing the words "regular closing days" described in Japanese on a paper sack of half-split chopsticks. At day 56 after the start of the treatment, she wrote a diary in "hiragana" Japanese characters, although a private teacher helped, such that "Today, I ate a bowl of rice topped with beef ("gyudon" in Japanese) as a school lunch, and Hanaki-san (her classmate's name in Japanese) ate rice balls", "Oomori-sensei (her teacher's name in Japanese), shall we go to a 'karaoka' shop next time?", and the like.

After 75 days, a teacher of her junior high school told that she recently began joking. Further, at 81 days thereafter, she answered by herself about 40 questions of addition on a workbook of a certain education organization in approximately 30 minutes. Moreover, she made all correct answers and provided each of all her answers with a circle mark as meaning that her answer was correct. For reference, the questions were as follows: "two plus one", "seven plus one", "twenty-three plus one", "twenty-four plus one", and the like.

At day 123 after treatment, she began to command a game machine "playstation DS" completely by herself, which was bought one year ago. After 130 days, she did not begin to utter groaning voices such as "woo, woo (in Japanese)" while she is stretching her neck and extending her arms. Moreover, she little gritted her teeth and showed any double folding phenomenon so that little paralyzed acts were considered to occur any more.

It should be noted herein that, at the time when the identical patient was once treated by low frequency electric currents in accordance with the same protocol six months ago before the treatment with the weak electric current, she made it conscious that the motor functions of her whole body were improved, although she could do or could not do addition up to the number of ten by herself. In the previous case, it was found that the current flow from the peripheral nerves to the central nerves could proceed toward normalization of the deep sensation. A rise in the muscle tone of the involuntary muscles means that the neural network associated with the deep sensation approached from its immature type to its mature type and the muscle tone could be adjusted unconsciously in the unconscious region. More speaking, it reveals that the unconscious adjustability of the muscle tone means a separation between the conscious region and the unconscious region and further the maturation of the neural network is caused to occur in the brain region involved in the separation of the conscious and unconscious regions. Moreover, the reorganization of the neural network by the flow of weak electric current, which accompanies an interval, is considered to be effective for the migraine that is considered to be caused by a lack of control in the neural network. Actually, there is the case that a 22-year-old female patient suffering from the migraine was cured by treatment within one week.

The following is a description regarding the case #2 of a 54-year-old male medical doctor. The doctor has managed approximately 250 medical fee bills in every month by checking names of diseases, medical points and so on and engaged in this work for 8 hours per day for approximately 3 days in one month, in addition to medical examination as daily work from 8 o'clock in the morning up to 8 o'clock in the night on days other than his days off. After medical examination, he was so exhausted that he could not check the medical fee bills so that he had to check the bills on his day off. Then, after finish of his medical examination, he underwent treatment by sending weak electric current to his face for 15 minutes and checked the medical fee bills for approximately 50 patients. As a result, it was found, surprisingly, that his work efficiency was improved by more than twice than before and completed the checking of the medical fee bills of about 50 patients within 1 to 2 hours. This indicates that the flow of the weak electric current through the head can remarkably improve the work and learning abilities.

Patients claiming synesthesia as a pathological condition and patients with the brain disorders such as Down's syndrome, mild mental retardation, autism, schizophrenia, depression, dementia, or the like may sometimes have abnormality of the somatic sensation including, for example, cutaneous sensation, etc. As abnormality of the neural network is considered to be present in the brain tissue corresponding to such pathological conditions, it is considered that the treatment method is effective which comprises the flow of the weak electric current accompanying intervals from the peripheral nerves to reorganize the neural network. The electric stimulation may be made on almost all the whole body surface if close to the sensory nerves. In the neurological diseases, there are generally recognized consciousness disorder, intelligent dysfunction, memory disorder, perceptual disorder, thought disorder, and disorder of emotion and mood.

As the neurological diseases for which the present invention is thought to be effective, there may be mentioned diseases as will be described below. As organic mental disorders such as symptomatic disorder or the like, there may be mentioned, for example, neurological diseases having a pathological change of the brain as can be seen by the naked eye, such as dementing disorder, Korsakoff syndrome, posttraumatic syndrome after head injury, etc. As disorders of mind and behavior by psychoactive substances, there may be mentioned, for example, diseases associated with psychoactive substances such as alcohol, opium, hemp, analgesics or hypnotics, cocaine, stimulants or caffeine, hallucinogenic drugs, cigarettes, volatile solutes, sugar, etc. These diseases may be broken down into dependency, abuse, addiction, and so on. They may also include alcohol dependency disease, drug dependency disease, etc. As schizophrenia, schizotypal disorder and paranoid disorder, there may include schizophrenia, schizotypal disorder, persistent paranoid disorder, acute and transient psychotic disorder, sensitive paranoid disorder, etc. As mood (mental) disorders including schizoaffective psychosis, there may be mentioned, for example, mood disorder (which may also be called emotional disorder in which the mood is mainly damaged), mania, bipolar disorder (which is also called manic-depressive psychosis), depression, etc.

As the neurotic disorders, stress-related disorders and somatoform disorders, there may be mentioned phobic anxiety disorders (e.g., agoraphobia, social (sociable) phobias, etc.), other anxiety disorders (e.g., panic disorder, generalized anxiety disorder, etc.), obsessive-compulsive disorder, etc. As severe stress disorders (disorders of response and adjustment to severe stress (in DSM-IV, the anxiety disorder includes PTSD and acute stress disorder, but in ICD-10, it is classified as severe stress response), there may be mentioned acute stress disorder, PTSD (post-traumatic stress disorder), adjustment disorder, dissociative (conversion) disorder (F44), dissociative disorder (almost corresponding to the dissociative disorder in DSM-IV-TR), other dissociative (conversion) disorders, multiple personality disorder (in DSM-IV-TR dissociative identity disorder), somatoform disorder (somatization disorder, hypochondrical disorder, persistent somatoform pain disorder, etc.), and other neurotic disorders.

As physiological disorders and behavior syndromes associated with somatic factors, there may be mentioned eating disorders, anorexia nervosa (anorexia), bulimia nervosa (bulimarexia), sleep disorder, insomnia, psychophysiologic insomnia (circadian rhythm sleep disorder, difficulty in sleeping, intermediate awakening, early morning awakening, hypersomnia, sleep apnea syndrome, narcolepsy, primary hypersomnia, repetitive hypersomnia, and idiopathic hypersomnia), parasomnia, REM sleep behavior disorder, sleepwalking, and pavor nocturnus.

As personality and behavior disorders, there may be mentioned particular personality disorders such as paranoid personality disorder, schizophrenia personality disorder, non-social personality disorder, emotionally unstable personality disorder (an impulsive type and a borderline type), histrionic personality disorder, compulsive personality disorder, anxiety (avoidant) personality disorder, dependent personality disorder, other specific personality disorders, personality disorder, personality disorders not otherwise specified, combined and other personality disorders, persistent personality changes, personality disorders not associated with brain injury and brain diseases, habit and impulsive disorders, gender identity disorder, sexual and gender disorders (e.g., fetishism, exhibitionism, voyeurism, pedophilia, sadism and masochism), psychological and behavioral disorders associated with sexual development and orienting, other adult personality and behavioral disorders, somatic or physiological disorders of intentional computation or camouflage of symptoms or disability (factitious disorders), Munchausen's syndrome, and personality and behavioral disorders not otherwise specified.

Mental disorders as mental retardation may include pervasive development disorder as physiological development disorder, autism, Asperger's syndrome, hyperactivity disorder (ADHD) (e.g., tic disorder, Tourette's syndrome, etc.) as disorders of behavior and emotion which develop normally in childhood and adolescence, hallucination, delusion and culture-bound syndrome (e.g., nervousness, anthrophobia, etc.) as other disorders.

Although it is described above by means of the embodiments, it is to be understood that the present invention is not limited whatsoever to them and any and all variations and modifications deviating from the above description are encompassed within the scope of the claims. For instance, the electric stimulation may be applied to the brain by gradually shifting the timing of applying stimulation (the timing of the first state) between the plural main electrodes from the synchronized state and re-synchronizing the timing of applying stimulation after a predetermined cycle, followed by repeating the above operations. Similarly, the timing of applying the electric stimulation may be shifted gradually between the main electrodes and the auxiliary electrodes from the synchronized state and then re-synchronized in a predetermined cycle, followed by repeating these operations. It should be understood as a matter of course that the present invention encompasses within the scope of the present invention the objects explicitly described herein as well as those impliedly described herein as having substantially the same and preferred embodiments and advantages as the present invention described above.

The electric stimulator according to the present invention is suitable and useful for improvements in functions of patients suffering from brain disorders.

DESCRIPTION OF REFERENCE SIGNS

1: main body (electric stimulator)
2A~2H: output parts
H: main electrodes
S: auxiliary electrodes
10: mounting means
12: extension parts

The invention claimed is:

1. An electric stimulator configured to apply electric signals to improve human brain dysfunction by accelerating neural network re-organization, the electric stimulator comprising:
   a plurality of main electrodes comprising a plurality of first patches, the plurality of first patches are configured to stick to at least two different particular sites on skin of a patient's body extending from the neck part to the head tip part selected from a temple site of the patient, a forehead site above eyes of the patient, a cheek site of the patient, and rear neck site of the patient for stimulating the brain without passage through the brain stem; and
   a plurality of auxiliary electrodes comprising a plurality of second patches, the plurality of second patches are configured to stick to skin of the patient's body that is lower than the neck;
   wherein the electric stimulator is configured to:
      repeatedly apply an electric signal to the body of the patient through the plurality of first patches in a predetermined cycle, the electric signal applied to the plurality of first patches is set for a weak electric current that stimulates the brain without passage through the brain stem and flows through the body of the patient; the weak electric current comprises a frequency of 10 to 80 pps (pulses per second) and a current value of 20 µA to 80 µA; the predetermined cycle comprises a first state and a second state, said first state being a state in which application of the weak electric current is continued for a fixed period of time and said second state being a state in which application of the weak electric current is ceased after the first state for a period of time equal to or longer than the above fixed period of time for the first state; wherein application of the weak electric current in the first state is configured to be applied to gradually increase the weak electric current toward a predetermined electric current value and then maintain the predetermined electric current value for a period of time longer than the predetermined period of time during which the weak electric current is increased gradually;
      apply an electric signal to the plurality of second patches, the electric signal applied to the plurality of second patches is set for a stimulating electric current larger than the weak electric current, the stimulating current configured to stimulate the brain with passage through the brain stem and flows through the body of the patient;
      wherein timing at which the electric signals are applied to the plurality of first patches and the plurality of second patches is set to gradually shift from synchronization and re-synchronize in a constant cycle; and
      wherein the application and timing of the electric signals improve human brain dysfunction by accelerating neural network re-organization.

2. The electric stimulator of claim 1, wherein the plurality of second patches of the plurality of auxiliary electrodes is configured to stick to the back of the patient to stimulate the brain through the spine.

3. The electric stimulator of claim 2, wherein the plurality of second patches of the plurality of auxiliary electrodes to which the electric stimulation is applied simultaneously is configured to stick on the back of the patient in a spatial relationship in a vertical direction and electric stimulation is configured to be applied by plural pairs of the auxiliary electrodes.

4. The electric stimulator of claim 1, wherein the stimulating current is from 30 mA to 300 mA.

* * * * *